United States Patent
Mascaux

(10) Patent No.: US 10,060,928 B2
(45) Date of Patent: Aug. 28, 2018

(54) METHOD FOR DETERMINING THE ENDOTOXIN CONTENT OF AN ALUMINUM SALT PREPARATION

(71) Applicant: GlaxoSmithKline Biologicals S.A., Rixensart (BE)

(72) Inventor: Clementine Mascaux, Wavre (BE)

(73) Assignee: GlaxoSmithKline Biologicals, S.A., Rixensart (BE)

( * ) Notice: Subject to any disclaimer, the term of this patent is extended or adjusted under 35 U.S.C. 154(b) by 243 days.

(21) Appl. No.: 14/896,473

(22) PCT Filed: Jun. 5, 2014

(86) PCT No.: PCT/EP2014/061652
§ 371 (c)(1),
(2) Date: Dec. 7, 2015

(87) PCT Pub. No.: WO2014/195387
PCT Pub. Date: Dec. 11, 2014

(65) Prior Publication Data
US 2016/0131652 A1 May 12, 2016

(30) Foreign Application Priority Data
Jun. 7, 2013 (GB) .................................. 1310151.4

(51) Int. Cl.
*G01N 33/579* (2006.01)
*G01N 33/20* (2006.01)
*G01N 33/569* (2006.01)
*A61K 39/00* (2006.01)

(52) U.S. Cl.
CPC ..... *G01N 33/579* (2013.01); *G01N 33/56911* (2013.01); *A61K 2039/55505* (2013.01); *G01N 33/20* (2013.01); *G01N 2400/50* (2013.01); *Y10T 436/25375* (2015.01)

(58) Field of Classification Search
CPC ..... A61K 2039/55505; G01N 2400/50; G01N 33/56911; G01N 33/579; G01N 33/20; Y10T 436/25; Y10T 436/25375
USPC ..................... 436/73, 94, 174, 177; 422/533
See application file for complete search history.

(56) References Cited

U.S. PATENT DOCUMENTS 5,876,955 A * 3/1999 Tamura ................ G01N 33/579
 435/18
6,365,147 B1 * 4/2002 Luo ....................... A61L 2/0011
 210/661

FOREIGN PATENT DOCUMENTS

WO 2009/081172 A1 7/2009

OTHER PUBLICATIONS

Fiske, et al., Method for reducing endotoxin in Moraxella catarrhalis UspA2 protein preparations, J. Chromatography B: Biomed. Sci. Applications, 753(2):269-278 (2001).
Park, et al., Comparison of the rabbit pyrogen test and Limulus amoebocyte lysate (LAL) assay for endotoxin in hepatitis B vaccines and the effect of aluminum hydroxide, Biologicals 33:145-151 (2005).
Magalhaes, et al., Methods of Endotoxin Removal from Biological Preparations: a Review, J. Pharm. Pharmaceut. Sci. 10(3):388-404 (2007).
Sharma, Endotoxin Detection and Elimination in Biotechnology, Biotechnol. Appl. Biochem. 8(1):5-22 (1986).
Yi Shi, et al.; "Detoxification of endotoxin by aluminum hydroxide adjuvant", Vaccine; Feb. 1, 2001; pp. 1747-1752; vol. 19.

* cited by examiner

*Primary Examiner* — Maureen Wallenhorst
(74) *Attorney, Agent, or Firm* — Virginia G. Campen

(57) ABSTRACT

Methods for determining the endotoxin content of an aluminum salt preparation for use in medicine are provided. The methods include mixing the aluminum salt with a desorption buffer and separating the aluminum salt from the endotoxin.

14 Claims, No Drawings

METHOD FOR DETERMINING THE ENDOTOXIN CONTENT OF AN ALUMINUM SALT PREPARATION

This application is filed pursuant to 35 U.S.C. § 371 as a United States National Phase Application of International Patent Application Serial No. PCT/EP2014/061652 filed Jun. 5, 2014, which claims priority to GB 1310151.4 filed Jun. 7, 2013, and the entire contents of each of the foregoing applications are hereby incorporated by reference.

FIELD OF THE INVENTION

The present invention provides a method of determining the endotoxin content in an aluminium salt preparation for use in medicine, in particular for use as an adjuvant in vaccines.

BACKGROUND TO THE INVENTION

Pyrogen or endotoxin (LAL) testing is required for parenteral drugs. Classical endotoxin assays cannot be used to test the endotoxin content of Aluminium salts. The endotoxin control added to the product is not recovered due to its property of interacting with the aluminium salt. Assay validity criteria require recovery and the ability to measure the control endotoxin in bulk aluminium concentrations. Given this interaction it is generally considered that the standard endotoxin tests are unsuitable for endotoxin testing in aluminium salt adjuvants. The only test that is suitable for determining endotoxin is the rabbit pyrogen test which involves injection of the aluminium salt into rabbits. Improved methods are required.

SUMMARY OF THE INVENTION

The present invention provides methods to accurately quantify the endotoxin in aluminium salt preparation. The invention provides methods for determining the endotoxin content of an aluminium salt preparation for use in medicine (in particular for use as an adjuvant in a vaccine), comprising the steps of:
  a) Mixing the aluminium salt with a desorption buffer thereby desorbing any endotoxin from the aluminium salt;
  b) Separating the aluminium salt from the endotoxin; and
  c) Measuring the amount of endotoxin.

The invention further provides methods of making a desorption buffer for use in a method for determining the endotoxin content of an aluminium salt preparation for use in medicine (in particular for use as an adjuvant in a vaccine), comprising the steps of:
  a) Mixing a base as defined herein, a metal chelating agent as defined herein and water; optionally
  b) Agitating the mixture (in particular for equal to or greater than 30 seconds, 1, 2, 3, 4, 5, 6, 7, 8, 9, 10, 11, 12, 13, 14 or 15 minutes); and optionally
  c) Incubating the mixture for equal to or greater than 5, 10, 15, 20, 25, or 30 minutes.

DETAILED DESCRIPTION

The present invention provides a method for determining the endotoxin content of an aluminium salt preparation for use in medicine (in particular for use as an adjuvant in a vaccine), comprising the steps of:
  a) Mixing the aluminium salt with a desorption buffer thereby desorbing any endotoxin from the aluminium salt;
  b) Separating the aluminium salt from the endotoxin; and
  c) Measuring the amount of endotoxin.

The present invention provides a method for determining the endotoxin content of an aluminium salt preparation for use in medicine (in particular for use as an adjuvant in a vaccine), comprising the steps of:
  a) Mixing the aluminium salt with a desorption buffer thereby desorbing any endotoxin from the aluminium salt;
  b) Centrifuging the mixture thereby separating the aluminium salt from the endotoxin; and
  c) Measuring the endotoxin content of the supernatant.

The present invention further provides a method for determining the endotoxin content of an aluminium salt preparation for use in medicine (in particular for use as an adjuvant in a vaccine), comprising the steps of:
  a) Mixing the aluminium salt with a desorption buffer thereby desorbing any endotoxin from the aluminium salt;
  b) Centrifuging the mixture thereby separating the aluminium salt from the endotoxin;
  c) Transferring the supernatant to apyrogenic receptacle; and
  d) Measuring the endotoxin content of said supernatant.

The term "Endotoxin" is used herein to mean that defined in the European Pharmacopeia 5.1.10 i.e. that endotoxin is considered as lipopolysaccharides (LPS) and/or lipooligosaccharides (LOS) derived from Gram negative bacteria.

Following the mixing step and prior to the separation/centrifugation step, the aluminium salt preparation and desorption buffer may be incubated in order to ensure that any endotoxin bound to the aluminium salt is desorbed. Accordingly, there is provided methods of the invention wherein the mixture aluminium salt and desorption buffer is incubated for greater than 1, 2, 3, 4, 5, 6, 7, 8, 9, 10, 11, 12, 13, 14, 15, 16, 17, 18, 19, 20, 21, 22, 23 or 24 hours. In particular embodiment the incubation period is less than 96 or 72 hours i.e. the incubation period is between 1 and 96 hours, 5 and 72 hours, 10 and 48 hours, 15 and 36 hours, or between 20 and 28 hours. In a particular embodiment, the mixture is no agitated during the incubation step.

The aluminium salt preparation and desorption buffer are suitably mixed at a ratio of between 1:9 and 9:1, for example 2:8, 3:7, 4:6, 5:5, 6:4, 7:2 or 8:2. In particular embodiments, the aluminium salt preparation and desorption buffer are mixed at a ratio of between 3:7, 4:6, 5:5, 6:4 7:3, in particular 4:6, 5:5 and 6:4.

The methods of the invention may be performed at any temperature that allows for desorption of endotoxin from the aluminium salt. Suitably, there is provided methods of the invention wherein said incubation is performed at between 10° C. and 70° C., for between example 20° C. and 65° C., 20° C. and 60° C., 15° C. and 30° C., between 17° C. and 28° C., between 19° C. and 26° C., between 21° C. and 23° C., or at about room temperature (about 22° C.).

The methods of the invention may comprise a step of agitating the mixture of aluminium salt and desorption buffer in order to ensure the desorption buffer is mixed with the aluminium composition. Suitably, there is provided methods of the invention wherein the mixture of aluminium salt and desorption buffer is agitated following step a) for more than 30 seconds, 40 seconds, 50 seconds, 1 minute, 1 minute 30 seconds or 2 minutes.

Any buffer that facilitates desorption of endotoxin may be used in the methods of the invention. Desorption buffers suitable for use in the present methods may be determined by exposing a candidate buffer to aluminium salt comprising a known amount of endotoxin (for example 20 EU/ml), incubating for approximately 24 hours+/−4 hours at room temperature, centrifuging at 10,000 rpm+/−1000 rpm for 10 minutes+/−1 min and then performing a LAL test on the supernatant. A buffer that desorbs between 50 and 200% of the endotoxin is considered a suitable desorption buffer.

There is provided methods of the invention wherein said desorption buffer comprises a salt and a metal chelating agent. Suitable salts are well known to the skilled person and include but are not limited to $Na_2HPO_4$. The $Na_2HPO_4$ is typically used in amount between 15% and 25%, for example about 18%, for example 17.8%, EDTA 0.224%, pH 8.0

In some embodiments, in particular wherein the methods of the invention are used to determine the endotoxin content of an aluminium hydroxide, the desorption buffer may comprise a further salt, for example NaCl. Where NaCl is used, typically the desorption buffer comprises between 5 and 250 mM NaCl.

Suitable metal chelating agents are well known to the skilled person and include but are not limited to EDTA (ethylenediaminetetraacetic acid). The EDTA typically used in amount between 0.2 and 0.3%, for example about 0.22%, for example 0.224%.

The desorption buffer may be at any pH that facilitates desorption of endotoxin from the aluminium salt. In one embodiment, the desorption buffer of the invention has a pH greater than pH 5.5, in particular when the desorption buffer used to desorb endotoxin from aluminium phosphate. There is provided method of the invention wherein said desorption buffer is between about pH7 and pH9. In a particular embodiment, there is provided a desorption buffer that is at about pH 8 (for example between pH 7.5 and 8.5)

In one embodiment, the desorption buffer of the invention has a pH greater than pH9.5, in particular when the desorption buffer is used to desorb endotoxin from aluminium hydroxide. There is provided method of the invention wherein said desorption buffer is between about pH9.5 and pH10.5. In a particular embodiment, there is provided a desorption buffer that is at about pH10. In a particular embodiment the pH is less than pH 10.5.

The desorption buffer may be at any temperature that prevents precipitation of one or more of the components of the buffer, in particular when stored at a concentrated for example between 1.5 and 2 times concentrate. Suitably, there is provided method of the invention wherein said desorption buffer is stored at a temperature of between about 30° C. and 45° C., 35° C. and 40° C., 36° C. and 38° C., or about 37° C.

The desorption buffer is ideally free of endotoxin, suitably there is provided methods of the invention wherein the desorption buffer is substantially free of endotoxin i.e. no endotoxin can be detected using any technique known to the skilled person.

The endotoxin is desorbed from the aluminium salt and suitably separated in order to allow testing of the endotoxin content. Separation may be performed using any method known to the skilled person. Suitably, there is provided methods of the invention wherein the mixture is centrifuged at a force required to pellet the aluminium salt and to maintain the endotoxin in the supernatant. In particular there are provided methods of the invention wherein the mixture of desorption buffer and aluminium salt are centrifuged at between 1000 and 1500×g, for example approximately 1118×g.

The desorbed endotoxin content may be measured according to any test available to the skilled person for measuring endotoxin. In particular, there is provided methods of the invention wherein the endotoxin content is measured. In particular, there is provided methods of the invention wherein the endotoxin content is quantified. Methods available and known to the skilled person include but are not limited to Limulus Amebocyte Lysate (LAL) assay, the Monocyte Activation Test or the EndoLISA method. In particular, the endotoxin is quantified in the methods of the invention by LAL (in particular by kinetic chromogenic method).

The methods of the invention may be used to determine the endotoxin content of any aluminium salt for use as an adjuvant in a vaccine. Suitable aluminium salt adjuvants are well known to the skilled person and include but are not limited to aluminium phosphate, aluminium hydroxide or a combination thereof. Suitable aluminium salt adjuvants include but are not limited to REHYDRAGEL™ HS, ALHYDROGEL™ 85, REHYDRAGEL™ PM, REHYDRAGEL™ AB, REHYDRAGEL™ HPA, REHYDRAGEL™ LV, ALHYDROGEL™ or a combination thereof. In particular, the methods of the invention are used to determine the endotoxin content of ADJUPHOS, REHYDRAGEL™ HS (3% aluminium hydroxide in water [General Chemical]) or ALHYDROGEL™ 85 (Brenntag BioSector [Denmark]).

In particular, the methods of the invention are used to determine the endotoxin content of aluminium salts that have a protein adsorption capacity of between 2.5 and 3.5, 2.6 and 3.4, 2.7 and 3.3 or 2.9 and 3.2, 2.5 and 3.7, 2.6 and 3.6, 2.7 and 3.5, or 2.8 and 3.4 protein (BSA)/ml aluminium salt. In a particular embodiment of the invention, the methods of the invention are used to determine the endotoxin content of an aluminium salt with the protein adsorption capacity of between 2.9 and 3.2 mg BSA/mg aluminium salt. Protein adsorption capacity of the aluminium salt can be measured by any means known to the skilled person. In a particular embodiment of the invention, the protein adsorption capacity of the aluminium salt is measured using the method as described in Example 1 of WO2012/136823 (which utilises BSA) or variations thereof.

The methods of the invention are used to determine the endotoxin content of aluminium salts described herein (i.e. having the protein adsorption capacity described herein) that have a crystal size of between 2.8 and 5.7 nm as measured by X-ray diffraction, for example 2.9 to 5.6 nm, 2.8 to 3.5 nm, 2.9 to 3.4 nm or 3.4 to 5.6 nm or 3.3 and 5.7 nm as measured by X-ray diffraction. X-ray diffraction is well known to the skilled person. In a particular embodiment of the invention the crystal size is measured using the method described in Example 1 of WO2012/136823 or variations thereof.

The methods of the invention are particularly useful in the quality control assays. The term "Quality control" assay is used herein to mean quality control (QC) is a procedure or set of procedures intended to ensure that a manufactured product or performed service adheres to a defined set of quality criteria or meets the requirements of the manufacturer. Accordingly, the methods of the invention are suitable for use in a quality control assay.

In a particular embodiment the methods of the invention described herein are used to test the aluminium salt preparation prior to formulation of the aluminium salt with other vaccine components. In a further embodiment the methods of the invention described herein are used to test the aluminium salt preparation following formulation of the aluminium salt with other vaccine components (for example particular antigens). In a further embodiment the methods of the invention described herein are used to test the aluminium salt preparation for endotoxin content both prior to and following formulation of the aluminium salt preparation with other vaccine components (for example antigens, in particular those described herein).

The methods of the invention may involve: extracting a sample from bulk of aluminium salt; testing the sample by the methods defined herein; and then if the sample passes the test, adsorbing one or more antigens (in particular those described herein) to said aluminium salt; and optionally combining said aluminium salt with one or more further antigens (in particular those described herein).

The aluminium salts of the invention may be formulated with antigens prior to and/or following testing of its endotoxin content.

Antigens that may be formulated with the aluminium salt of the invention include but are not limited to tetanus toxoid (TT), diphtheria toxoid (DT), Hepatitis B surface antigen, Inactivated polio virus (IPV), Pertactin, with filamentous haemagglutinin (FHA) Pertussis toxoid and/or *Haemophilus influenzae* type B polysaccharide (Hib) [in particular, the polyribosyl ribitol phosphate capsular saccharide (PRP) from *H. influenzae* type B), Human Papilloma Virus (e.g. virus like particle from HPV 6, 11, 16, 18 or a combination thereof), polysaccharides derived from *Streptococcus pneumoniae* conjugated to a carrier protein, for example TT, DT and/or CRM197.

Tetanus toxoids (TT) and their methods of preparation are well known in the art. TT may be produced by purification of the toxin from a culture of *Clostridium tetani* followed by chemical detoxification, but it is alternatively made by purification of a recombinant, or genetically detoxified, analogue of the toxin (for example, as described in EP 209281). A preferred method of detoxification is as follows. Following fermentation, the broth is filtered on a 0.1-0.3 μm filter in the presence of Diatomite as filter aid. The harvest is clarified through a 0.22 μm filter, concentrated and diafiltered on 30 kD flatsheet membranes against 10 volumes of phosphate buffer (20 mM pH 7.3). The diafiltered toxin is then detoxified for 4 weeks at 37° C. in the following conditions: formaldehyde 20 mM-lysine 3 mM-potassium phosphate 100 mM-initial pH 7.3-500 Lf/ml. The resulting toxoid is purified by ammonium sulfate fractionation, concentrated and diafiltered (30 kD) against WFI to remove ammonium sulfate. NaCl is added to a final concentration of 0.9%, the pH is adjusted to 7.3 and the purified tetanus toxoid is sterile filtered.

Any suitable tetanus toxoid may be used. 'Tetanus toxoid' may encompass immunogenic fragments of the full-length protein (for instance Fragment C—see EP 478602).

The tetanus toxoid of the invention is typically adsorbed onto an aluminium salt. In a particular embodiment of the invention the aluminium salt is aluminium hydroxide. In another embodiment, the tetanus toxoid of the invention may be adsorbed onto an aluminium salt such as aluminium phosphate. In a further embodiment the tetanus toxoid may be adsorbed onto a mixture of both aluminium hydroxide and aluminium phosphate.

Methods of adsorbing protein including tetanus toxoids onto aluminium salts are well known to the skilled person (for example vaccine preparation is generally described in Vaccine Design "The subunit and adjuvant approach" (eds Powell M. F. & Newman M. J.) (1995) Plenum Press New York).

Diphtheria toxoids (DT) and their methods of preparation are well documented. Any suitable diphtheria toxoid may be formulated with the aluminium salt described herein following or prior to endotoxin testing. For instance, DT may be produced by purification of the toxin from a culture of *Corynebacterium diphtheriae* followed by chemical detoxification, but is alternatively made by purification of a recombinant, or genetically detoxified analogue of the toxin (for example, CRM197, or other mutants as described in U.S. Pat. No. 4,709,017, U.S. Pat. No. 5,843,711, U.S. Pat. No. 5,601,827, and U.S. Pat. No. 5,917,017). A preferred method of detoxification is as follows. Following fermentation, the Diphtheria toxin is harvested by TFF 0.45 μm, clarified through a 0.22 μm filter, concentrated and diafiltered on 10 kD flatsheet membranes against 10 volumes of phosphate buffer (20 mM-pH 7.2). The diafiltered toxin is then detoxified for 6 weeks at 37° C. in the following conditions: formaldehyde 50 mM-lysine 25 mM-potassium phosphate 50 mM-initial pH 7.2-300 Lf/ml. The resulting toxoid is purified by ammonium sulfate fractionation, concentrated and diafiltered (30 kD) against WFI to remove ammonium sulfate. NaCl is added to a final concentration of 0.9%, the pH is adjusted to 7.3 and the purified diphtheria toxoid is sterile filtered.

The inactivated polio vaccine (IPV) may comprise IPV type 1 or IPV type 2 or IPV type 3, or IPV types 1 and 2, or IPV types 1 and 3, or IPV types 2 and 3, or IPV types 1, 2 and 3.

Methods of preparing inactivated poliovirus (IPV) are well known in the art. In one embodiment, IPV should comprise types 1, 2 and 3 as is common in the vaccine art, and may be the Salk polio vaccine which is inactivated with formaldehyde (see for example, Sutter et al., 2000, Pediatr. Clin. North Am. 47:287; Zimmerman & Spann 1999, Am Fam Physician 59:113; Salk et al., 1954, Official Monthly Publication of the American Public Health Association 44(5):563; Hennesen, 1981, Develop. Biol. Standard 47:139; Budowsky, 1991, Adv. Virus Res. 39:255). Alternatively, IPV may be made using Sabin strains (Sabin-IPV; Kersten at al (1999), Vaccine 17:2059).

In one embodiment the IPV is not adsorbed (e.g. before mixing with other components). In another embodiment, the IPV component(s) of the invention may be adsorbed onto an aluminium salt such as aluminium hydroxide (e.g. before or after mixing with other components). In another embodiment, the IPV component(s) of the invention may be adsorbed onto an aluminium salt such as aluminium phosphate. In a further embodiment the IPV component(s) may be adsorbed onto a mixture of both aluminium hydroxide and aluminium phosphate. If adsorbed, one or more IPV components may be adsorbed separately or together as a mixture. In a further embodiment, the IPV is adsorbed onto an aluminium salt/particle as described herein.

Pertactin (the 69 kDa antigen of pertussis) is an outer membrane protein which is heat-stable and can be prepared by methods known in the art (see EP0162639). The pertactin is optionally adsorbed onto an aluminium salt particle. In one embodiment of the invention the pertactin is adsorbed to aluminium hydroxide. In a particular embodiment of the invention, the pertactin is adsorbed onto an aluminium salt as described herein.

Filamentous haemagglutinin (FHA) can be prepared in methods well known in the art (see methods disclosed and referenced in WO/1990/013313 (U.S. Pat. No. 7,479,283)).

The FHA is optionally adsorbed onto an aluminium salt particle. In one embodiment of the invention the FHA is adsorbed to aluminium hydroxide. In a particular embodiment of the invention, the FHA is adsorbed onto an aluminium salt as described herein.

Methods of producing pertussis toxoid are well known to the skilled person. Pertussis toxin may be detoxified by a well known method of formaldehyde treatment or by means of mutations (PT derivative). Substitutions of residues within the S1 subunit of the protein have been found to result in a protein which retains the immunological and protective properties of the pertussis toxin, but with reduced or no toxicity (EP 322533). The detoxifying mutations discussed in the claims of EP322533 are examples of the PT detoxified mutants of the present invention. The pertussis toxoid is optionally adsorbed onto an aluminium salt particle. In one embodiment of the invention the pertussis toxoid is adsorbed to aluminium hydroxide. In a particular embodiment of the invention, the pertussis toxoid is adsorbed onto an aluminium salt as described herein.

The polyribosyl ribitol phosphate capsular saccharide (PRP) from *Haemophilus influenzae* type b may be conjugated to a carrier protein. The saccharide is a polymer of ribose, ribitol and phosphate. The Hib antigen may optionally be adsorbed onto aluminium phosphate as described in WO97/00697, or may be unadsorbed as described in WO02/00249 or may not have undergone a specific process of adsorption.

By an antigen being 'unadsorbed onto an aluminium adjuvant salt' ("unadsorbed" or "not adsorbed") herein it is meant for example that an express or dedicated adsorption step for the antigen on fresh aluminium adjuvant salt is not involved in the process of formulating the composition.

Hib may be conjugated to any carrier which can provide at least one T-helper epitope, and may be tetanus toxoid, diphtheria toxoid, CRM-197 (diphtheria toxin mutant) or Protein D from non-typeable *H. influenzae* (EP0594610).

In a further embodiment, there is provided a process of the invention further comprising the step of formulating the immunogenic composition with a hepatitis B surface antigen.

The preparation of Hepatitis B surface antigen (HBsAg) is well documented. See for example, Hartford et al., 1983, Develop. Biol. Standard 54:125; Gregg et al., 1987, Biotechnology 5:479; EP0226846; EP0299108. It may be prepared as follows. One method involves purifying the antigen in particulate form from the plasma of chronic hepatitis B carriers, as large quantities of HBsAg are synthesised in the liver and released into the blood stream during an HBV infection. Another method involves expressing the protein by recombinant DNA methods. The HBsAg may be prepared by expression in the *Saccharomyces cerevisiae* yeast, pichia, insect cells (e.g. Hi5) or mammalian cells. The HBsAg may be inserted into a plasmid, and its expression from the plasmid may be controlled by a promoter such as the "GAPDH" promoter (from the glyceraldehyde-3-phosphate dehydrogenase gene). The yeast may be cultured in a synthetic medium. HBsAg can then be purified by a process involving steps such as precipitation, ion exchange chromatography, and ultrafiltration. After purification, HBsAg may be subjected to dialysis (e.g. with cysteine). The HBsAg may be used in a particulate form.

As used herein the expression "Hepatitis B surface antigen" or "HBsAg" includes any HBsAg antigen or fragment thereof displaying the antigenicity of HBV surface antigen. It will be understood that in addition to the 226 amino acid sequence of the HBsAg S antigen (see Tiollais et al., 1985, Nature 317:489 and references therein) HBsAg as herein described may, if desired, contain all or part of a pre-S sequence as described in the above references and in EP0278940. In particular, the HBsAg may comprise a polypeptide comprising an amino acid sequence comprising residues 133-145 followed by residues 175-400 of the L-protein of HBsAg relative to the open reading frame on a Hepatitis B virus of ad serotype (this polypeptide is referred to as L*; see EP0414374). HBsAg within the scope of the invention may also include the preS1-preS2-S polypeptide described in EP0198474 (Endotronics) or analogues thereof such as those described in EP0304578 (McCormick and Jones). HBsAg as used herein can also refer to mutants, for example the "escape mutant" described in WO 91/14703 or EP0511855A1, especially HBsAg wherein the amino acid substitution at position 145 is to arginine from glycine.

The HBsAg may be in particle form. The particles may comprise for example S protein alone or may be composite particles, for example L*, S) where L* is as defined above and S denotes the S-protein of HBsAg. The said particle is advantageously in the form in which it is expressed in yeast.

In one embodiment, HBsAg is the antigen used in ENGERIX B™ (GlaxoSmithKline Biologicals S.A.), which is further described in WO93/24148.

Hepatitis B surface antigen may optionally be adsorbed onto an aluminium salt, in particular aluminium phosphate, which may be done before mixing with the other components (described in WO93/24148).

The Hepatitis B component should be substantially thiomersal free (method of preparation of HBsAg without thiomersal has been previously published in EP1307473).

The present invention further provides methods of making a desorption buffer for use in a method for determining the endotoxin of an aluminium salt comprising the steps of:
 a) Mixing one or more salts as defined herein, a metal chelating agent as defined herein and water; optionally
 b) Agitating the mixture (in particular for equal to or greater than 30 seconds, 1, 2, 3, 4, 5, 6, 7, 8, 9, 10, 11, 12, 13, 14 or 15 minutes); and optionally
 c) Incubating the mixture for equal to or greater than 5, 10, 15, 20, 25, or 30 minutes.

The present invention further provides methods of making a desorption buffer for use in a method for determining the endotoxin of an aluminium salt comprising the steps of:
 a) Mixing a salt, a metal chelating agent and water; optionally
 b) Agitating the mixture combined to incubation periods at 37° C.+/−1° C. (to dissolve); and optionally
 c) Adding an acid or a base to fix the pH
 d) Adding water to reach the final volume of the preparation; optionally
 e) Storing at 37° C.+/−1° C.

Steps a) and b) may be performed more than once, there is provided methods of making a desorption buffer as defined herein wherein steps b) and/or c) are repeated 1, 2 or more times.

There is provided methods of making a desorption buffer as defined wherein the water is substantially free of endotoxin.

There is provided methods of making a desorption buffered as defined wherein the water of step a) is preheated to about 30° C. and 45° C., 35° C. and 40° C., 36° C. and 38° C., or about 37° C. (±1° C.).

There is provided methods of making a desorption buffer as defined wherein the pH is adjusted to between 7 and 9, in particular about pH 8. Any acid may be used to adjust that pH whilst not affecting the ability of the desorption buffer to desorb endotoxin from the aluminium salt. In particular HCl may be used to adjust the pH in the manufacture of desorption buffers described herein. In particular the pH is adjusted when the buffer is at about 30° C. and 45° C., 35° C. and 40° C., 36° C. and 38° C., or about 37° C. (±1° C.). Any suitable base or acid may be used to adjust that pH whilst not affecting the ability of the desorption buffer to desorb endotoxin from the aluminium salt.

There is provided methods of making a desorption buffer as defined herein further comprising the step of d) storing the desorption buffer at about 30° C. and 45° C., 35° C. and 40° C., 36° C. and 38° C., or about 37° C. (±1° C.).

The terms "comprising", "comprise" and "comprises" herein are intended by the inventors to be optionally substitutable with the terms "consisting of", "consist of" and "consists of", respectively, in every instance.

The term "about" used herein is intended to mean the amount±10%.

EXAMPLES

1. Preparation of Desorption Buffer:

In order to make 100 ml desorption buffer 17.8 g $Na_2HPO_4$, 0.224 g EDTA and 90 ml of pyrogen-free water (if possible preheated in a 37° C. incubator) was placed in a 250 ml Nunc pyrogen-free container.

The salt and EDTA was dissolved by agitating 15 min on agitating table, heating 30 min in incubator at 37° C.±1° C. and repeating the agitation and heating until fully dissolved.

To adjust the pH 3 ml HCl 1N was added, the pH is measured and adjusted to pH 8.0 with HCl 1N if necessary. The volume is made up to 100 ml with pyrogen-free water. The absence of endotoxin was determined by LAL analysis at 1/100 dilution. The desorption buffer was stored at 37° C.±1° C.

2. Determination of Endotoxin:

In order to determine the endotoxin content of an aluminium sample (4 ml) desorption buffer (6 ml) was added to the aluminium salt sample. The mixture was agitated for 1 minute and then incubated at room temperature for 24 hours.

After the incubation, the mixture is shaken slowly by turning to tube upside down 5 times. A sample (1.5 ml) is removed and transferred to a 2 ml eppendorf tube. The mixture was centrifuged at 10,000 rpm for 10 minutes. The supernatant was then transferred to a pyrogen-free tube. The endotoxin content was then quantified using the LAL by kinetic chromogenic method at 1/50 dilution.

The invention claimed is:

1. A method for measuring endotoxin content in an aluminium salt preparation for use in medicine, comprising the steps of:
    a. Extracting a sample from a bulk aluminium salt preparation,
    b. Mixing the sample with an aqueous desorption buffer comprising a salt and a metal chelating agent to provide a mixture, thereby desorbing any endotoxin from the aluminium salt;
    c. Separating the aluminium salt from the aqueous mixture; and
    d. Measuring endotoxin content in the aqueous mixture.

2. The method according to claim 1 wherein step (c) comprises centrifuging the aqueous mixture to provide a pellet of aluminium salt and a supernatant, and step (d) measures endotoxin content in the supernatant.

3. The method according to claim 2 wherein the sample of aluminium salt preparation and the desorption buffer are mixed at a ratio of between 1:9 and 9:1.

4. The method according to claim 3 wherein the aqueous mixture is incubated after step (b) and before step (c) between 1 and 96 hours.

5. A method according to claim 4 wherein said incubation is performed at about 22° C.

6. The method according to claim 1 wherein said desorption buffer comprises a salt selected from $Na_2HPO_4$ and NaCl.

7. A method according to claim 6 wherein the desorption buffer comprises a further salt.

8. The method according to claim 6 wherein said desorption buffer has a pH equal to or greater than pH5.5.

9. The method according to claim 6 wherein said desorption buffer is at a temperature of between about 30° C. and 45° C.

10. The method according to claim 6 wherein said desorption buffer salt is $Na_2HPO_4$ and said metal chelating agent is EDTA.

11. The method according to claim 10 wherein the $Na_2HPO_4$ is between 15 and 20% by weight and EDTA is between 0.2 and 0.3% by weight.

12. The method according to claim 1 wherein the desorption buffer is substantially free of endotoxin.

13. The method according to claim 1 wherein endotoxin content is measured by Limulus Amebocyte Lysate (LAL) assay.

14. The method according to claim 1 wherein the aluminium salt is aluminium phosphate, aluminium hydroxide or a combination thereof.

* * * * *